United States Patent [19]
Hart

[11] Patent Number: 6,030,394
[45] Date of Patent: Feb. 29, 2000

[54] VESSEL LOOP WITH TRACTION-ENHANCING SURFACE

[75] Inventor: Charles C. Hart, Huntington Beach, Calif.

[73] Assignee: Applied Medical Resources Corporation, Laguna Hills, Calif.

[21] Appl. No.: 09/031,327

[22] Filed: Feb. 26, 1998

[51] Int. Cl.[7] .................................................. A61B 17/08
[52] U.S. Cl. ............................ 606/151; 606/203; 623/12
[58] Field of Search .................................... 606/151, 203, 606/158, 157, 194, 195; 623/1, 12; D24/143, 133

[56] References Cited

U.S. PATENT DOCUMENTS

| | | | |
|---|---|---|---|
| 3,726,279 | 4/1973 | Barefoot et al. | 128/327 |
| 4,578,080 | 3/1986 | Helal | 623/13 |
| 4,854,316 | 8/1989 | Davis | 128/334 R |
| 5,074,873 | 12/1991 | Dioguardi | 606/203 |
| 5,171,253 | 12/1992 | Klieman | 606/158 |
| 5,368,602 | 11/1994 | de la Torre | 606/151 |
| 5,522,822 | 6/1996 | Phelps et al. | 606/151 |
| 5,540,714 | 7/1996 | Payne, Jr. et al. | 606/203 |

FOREIGN PATENT DOCUMENTS

| | | | |
|---|---|---|---|
| 2035 607 | 1/1972 | Germany | 335/12 |
| 0668675 | 9/1977 | U.S.S.R. . | |
| WO 8303345 | 10/1983 | WIPO | 606/158 |

*Primary Examiner*—Michael Buiz
*Assistant Examiner*—Lien Ngo
*Attorney, Agent, or Firm*—Richard L. Myers

[57] ABSTRACT

A vessel loop adapted to frictionally engage a vessel of a patient includes an elongate elastomeric member having an outer surface which is adapted to be brought into contact with the vessel. A friction-enhancing structure is disposed relative to this outer surface to increase the frictional relationship between the elongate member and the vessel. The friction-enhancing structure may take the form of a woven or non-woven mesh, various projections, bristles, or granules, for example. A woven mesh sleeve is disposed over the elongate member and bonded to the member in a preferred embodiment.

16 Claims, 3 Drawing Sheets

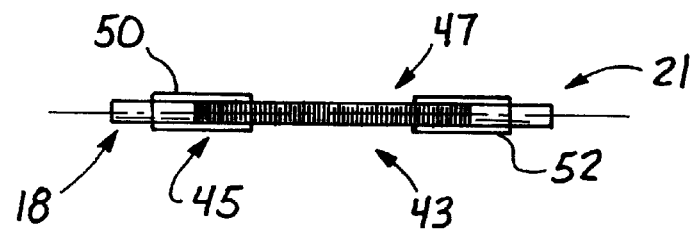
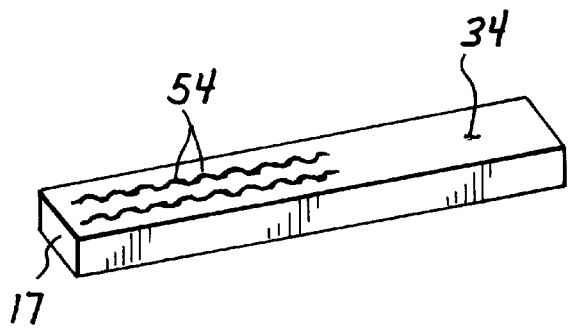
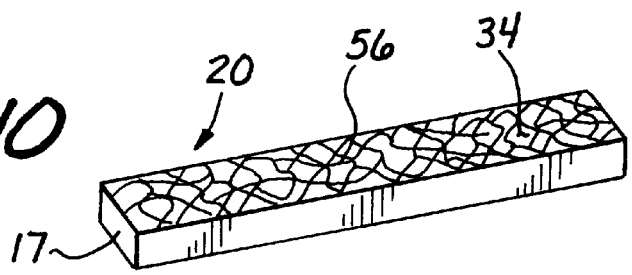
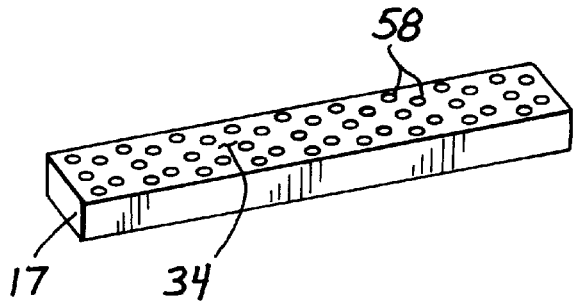
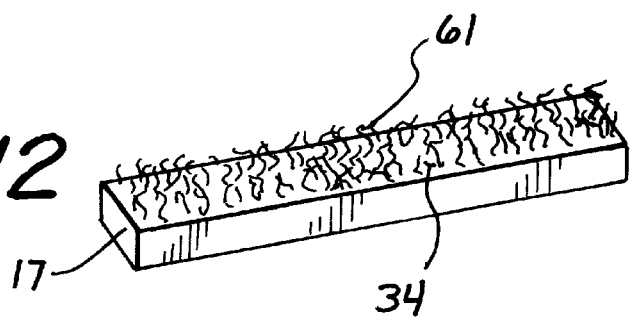

6,030,394

VESSEL LOOP WITH TRACTION-ENHANCING SURFACE

BACKGROUND OF THE INVENTION

1. Field of the Invention

This invention relates generally to surgical devices for manipulating or occluding body conduits of a patient, and more specifically to vessel loops adapted to manipulate blood vessels in a patient.

2. Discussion of the Prior Art

Particularly in vascular surgery it is often advantageous to manipulate a blood vessel, for example, by engaging the vessel and holding it away from its surrounding tissue bed. This not only improves access to the vessel but also to the tissue bed, as may be required by a particular surgical operation. In the past, vessel loops have been used for this purpose. These loops have been formed from elastomeric materials and provided with a generally elongate configuration. Positioning the loop around the vessel provides suitable engagement with the vessel and enables the ends of the loop to be brought into proximity where they can be pulled to space the vessel from the surrounding tissue bed.

In an operation where the vessel itself is the operative site, two vessel loops are commonly used, one on either side of the operative site, to space the vessel from the tissue bed. Particularly in the this attitude, migration of the vessel loops has been a problem as they tend to slide toward each other thereby obscuring the operative site. This undesirable migration of the vessel loops has been compounded by the generally wet surface of the vessel, which has provided a relatively low coefficient of friction between the vessel and the loop.

SUMMARY OF THE INVENTION

In order to inhibit this undesirable migration, the vessel loop of the present invention is provided with an irregular surface. More specifically, the elastic elongate element forming the loop has an outer surface which is provided with the irregular configuration. This greatly enhances the coefficient of friction with the vessel, thereby increasing the traction between the vessel loop and the vessel. With this increased traction, the vessel loop tends to maintain its desired position along the vessel. The irregular surface can also be relied upon to enhance use of the vessel loop for the purposes of occlusion.

In a preferred embodiment, the irregular surface of the vessel loop is provided by a mesh structure which is disposed to extend outwardly of the outer surface of the elongate element forming the loop. This mesh can be provided in the form of a sleeve surrounding the elongate element. The sleeve can be bonded to the element, for example by adhesion, heatsealing, or overmolding.

DESCRIPTION OF THE DRAWINGS

FIG. 8 is a side-elevation view of a further embodiment of the vessel loop wherein the ends of the mesh sleeve are held in a fixed relationship with the elongate member by overmolded hubs;

FIG. 9 is a perspective view of a vessel loop including an improved traction surface with projections;

FIG. 10 is a perspective view of a vessel loop with an improved traction surface including a non-woven mesh;

FIG. 11 is a perspective view of a vessel loop with an improved traction surface including granules; and FIG. 12 is a perspective view of a vessel loop with an improved traction surface including bristles.

DESCRIPTION OF THE PREFERRED EMBODIMENTS AND BEST MODE OF THE INVENTION

Figure 1:
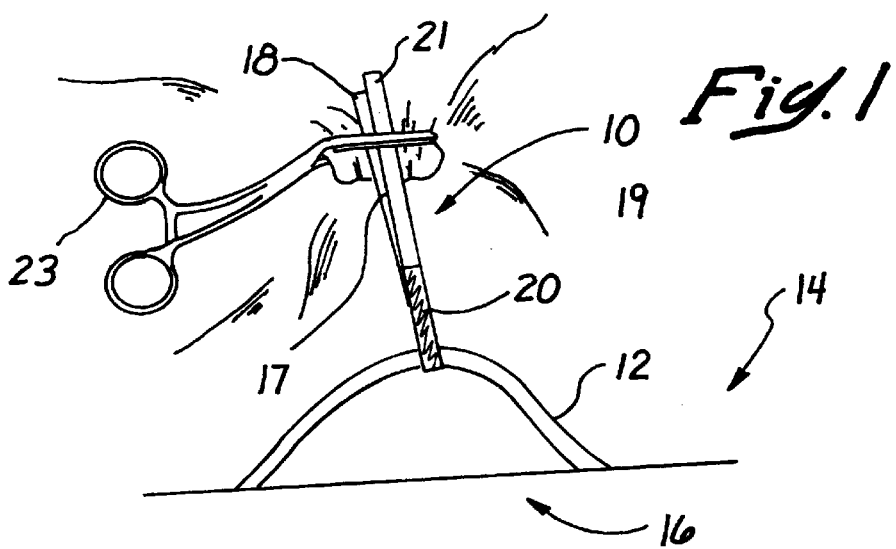
FIG. 1 is a perspective view of a vessel engaged and withdrawn from its surrounding tissue by a vessel loop of the present invention clamped to a drape of the patient.

A vessel loop of the present invention is illustrated in FIG. 1 and designated generally by the reference numeral 10. The vessel loop 10 is operatively disposed in a surgical operation wherein a vessel 12 of a patient 14 is engaged by the loop 10 and removed from its surrounding tissue bed 16. The vessel loop 10 in this embodiment includes an elongate member 17 extending between ends 18 and 21. This elongate member 17 will typically have elastomeric properties and may be formed, for example, from latex or rubber. The elongate member 17 has an outer surface 19, at least a portion of which is covered with a traction-enhancing structure such as a mesh 20. In use, the loop 10 is wrapped at least partially around the vessel 12 and its ends 18 and 21 brought into proximity. These ends can then be pulled to space the vessel 12 from its surrounding tissue bed 16. When it is desirable to maintain this space relationship, the ends 18 and 21 of the loop 10 can be held by a clamp 23 and attached to a drape 25.

Figure 2:
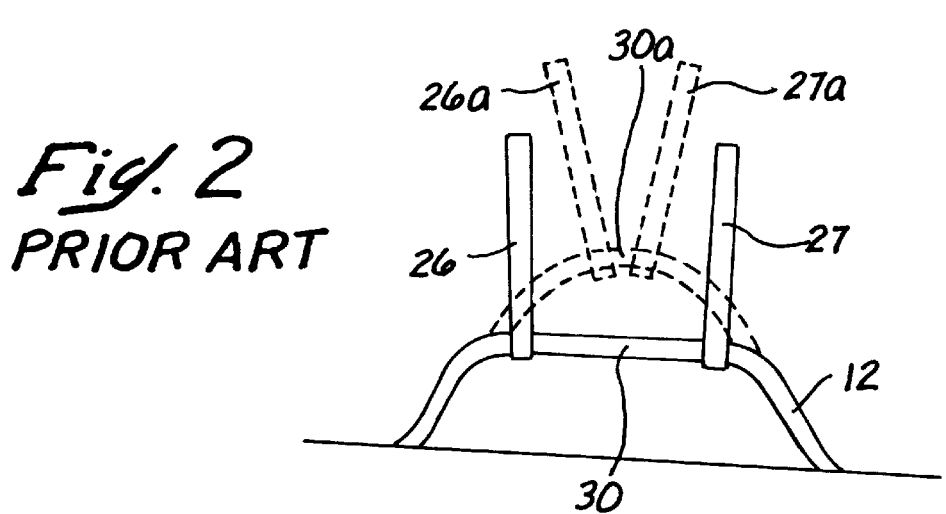
FIG. 2 is a side elevation view illustrating use of a pair of vessel loops of the prior art to isolate an operative site on the vessel.

Vessel loops, such as the loop 10, are often used in combination particularly where the vessel 12 is the operative site of interest. In FIG. 2, a vessel loop 26 of the prior art is used in combination with a vessel loop 27. These loops 26 and 27 engage the vessel 12 at spaced locations on either side of an operative site 30 of the vessel 12. This use of the loops 26 and 27 is intended to provide a higher degree of stability and isolation of the operative site 30 free of interference by the vessel loops 26 and 27.

This configuration dramatically illustrates the problem with vessel loops of the past which have tended to migrate along the vessel 12. Particularly in this tandem configuration, the vessel loops 26 and 27 have tended to migrate toward each other as illustrated by the dotted lines 26a and 27a in FIG. 2. This migration has not only tended to elevate the vessel 12 as shown by the dotted lines 12a, but also tended to bring the vessel loops 26a and 27a into an interfering relationship with the operative site 30a.

Failure of a vessel loop in any configuration to maintain its initial position can be distracting, annoying, and frustrating to the surgeon who would prefer to maintain focus on the operative site 30.

Figure 3:
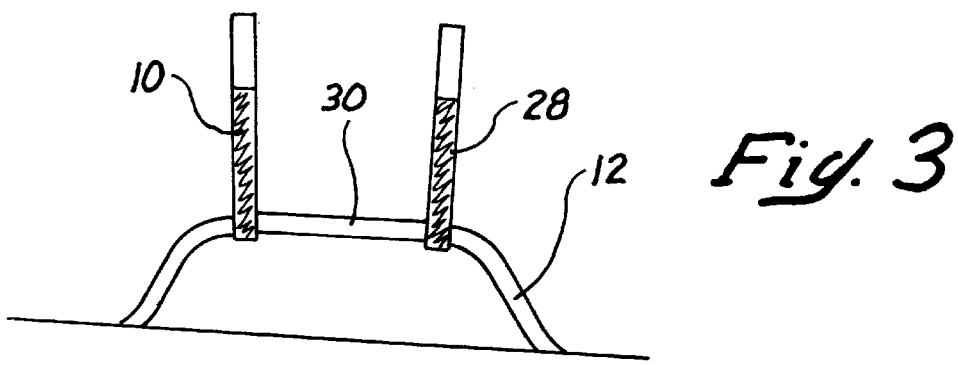
FIG. 3 is a side elevation view of a pair of vessel loops of the present invention which provide increased traction and thereby inhibit migration relative to the vessel.

By comparison, FIG. 3 illustrates the vessel loop 10 and a second vessel loop 28 of the present invention, where improved traction between the loops 10, 28 and the vessel 12 inhibit migration and promote isolation of the operative site 30.

Figure 4:
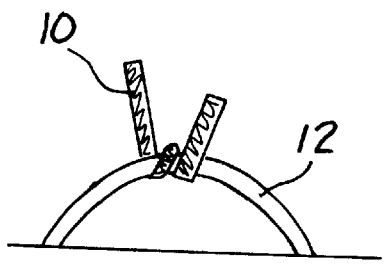
FIG. 4 is a side elevation view of a vessel loop surrounding the vessel to provide even further traction and facilitate occlusion of the vessel.

The vessel loop 10 can also be used to occlude the vessel 12. This is typically accomplished by totally surrounding the vessel 12 in a loop configuration, as illustrated in FIG. 4. Pulling on the ends 18, 21 of the vessel loop 10 can draw the loop tightly about the vessel 12 resulting in its occlusion.

Figure 5:
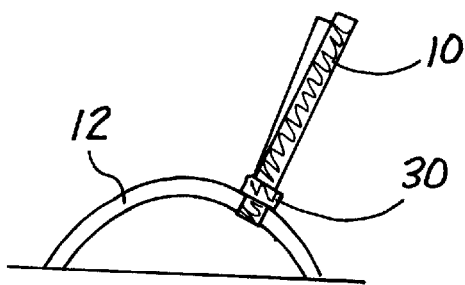
FIG. 5 is a side elevation view of the vessel loop in combination with a friction ring which facilitates occlusion of the vessel.

Another method of occlusion involves a friction ring 30 best illustrated in FIG. 5. This ring 30 can be slid over the ends 18, 21 of the vessel loop 10 and pushed down tightly against the vessel 12. A significant frictional relationship between the ring 30 and the vessel loop 10 will maintain this type of occluding relationship.

Figure 6:
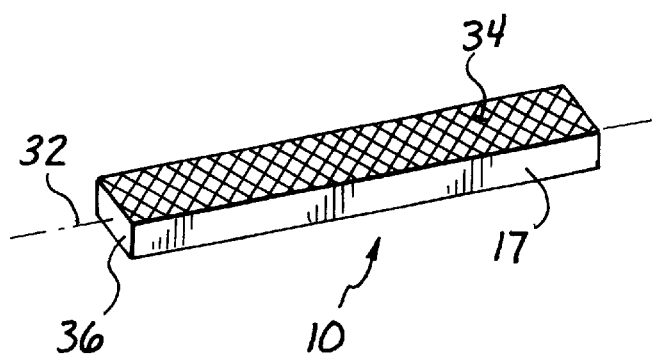
FIG. 6 is a perspective view of one embodiment of the vessel loop including an elastomeric elongate member and a mesh disposed on a portion of its outer surface.

Several embodiments of the vessel loop 10 are contemplated, each providing enhanced traction characteristics which inhibit migration. In the embodiment of FIG. 6, the elongate elastomeric member 17 has an axis 32 and a generally rectangular configuration in radial cross-section. Thus, the elongate member 17 is defined by a pair of opposing major surfaces 34 and 36 which extend along the length of the member 17. One of these major surfaces will typically be brought into contact with the vessel 12 when the loop 10 is operatively positioned. It is this contacting surface 34 which preferably is provided with a structure that increases the frictional relationship between the loop 10 and the vessel 12. In the illustrated embodiment this structure includes the mesh 20 which can either be embedded in or disposed on the surface 34. In a preferred embodiment, the mesh 20 is bonded to at least the surface 34, for example, by adhesion using a glue 38.

Figure 7:
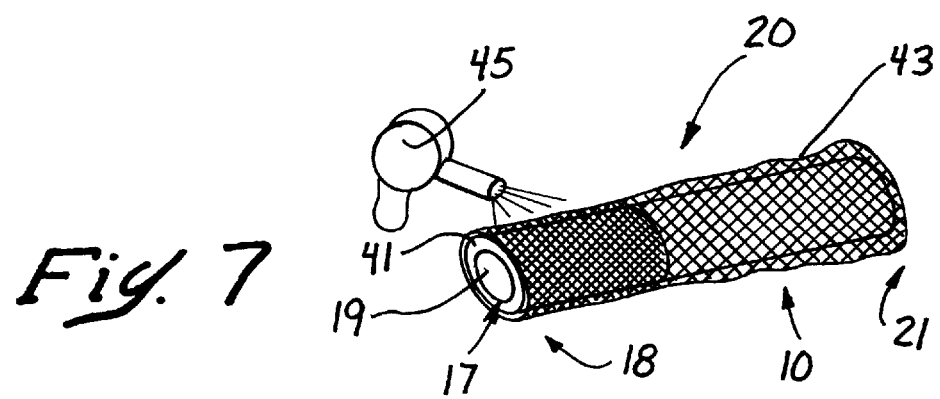
FIG. 7 is a perspective view of another embodiment of the vessel loop wherein the mesh is formed as a sleeve and heatsealed to the elongate element.

Another embodiment of the vessel loop 10 is illustrated in FIG. 7. In this embodiment, the elongate member 17 has the configuration of a hollow cylinder 41, and the mesh 20 is provided in the form of a cylindrical sleeve 43 which surrounds the cylinder 41. It has been found that the greatest traction is achieved where the sleeve 43 is not embedded in the outer surface 19 of the elongate member 17. To achieve this preferred orientation, the mesh 20 can be bonded to the elongate member 17 by a process of heatsealing which will typically involve use of a heat gun 45. This heatsealing tends to melt the mesh 20 into the outer surface of the elongate member 17. As a consequence, the heatsealing may be restricted to the ends 18 and 21 of the loop 10.

In a further embodiment of the invention, the sleeve 43 is provided with ends 45 and 47, which define a length less than that of the elongate member 17. As a result, the ends 45 and 47 of the sleeve 43 are disposed inwardly of the ends 18 and 21 of the elongate member 17. In such an embodiment, the sleeve can be held in place by a pair of hubs 50, 52 which are overmolded bonding the ends 45 and 47 of the sleeve 43 to the elongate member 17.

It will be noted that the traction of the vessel loop 10 can be increased with several embodiments in addition to those containing the mesh 20. One such embodiment is illustrated in FIG. 9 where the outer surface 34 of the elongate member 17 is provided with projections 54, which may be arranged in a random order or an ordered waffle configuration. These projections 54 greatly increase the coefficient of friction between the elongate member 17 and the vessel 12.

In a further embodiment illustrated in FIG. 10, the mesh 20 is formed of a single monofilament which is formed as a non-woven mesh 56. In this case, the non-woven mesh 56 can be adhered or otherwise bonded to the elongate member 17 in any of the manners previously discussed.

Granules 58 can also be disposed on the surface 34 of the elongate member 17, as illustrated in FIG. 11. A further embodiment illustrated in FIG. 12 contemplates the use of bristles 61 on the surface 34 in order to facilitate the frictional relationship between the vessel loop 10 and the vessel 12.

It will be understood that many other modifications can be made to the various disclosed embodiments without departing from the spirit and scope of the concept. For example, various sizes of the surgical device are contemplated as well as various types of constructions and materials. It will also be apparent that many modifications can be made to the configuration of parts as well as their interaction. For these reasons, the above description should not be construed as limiting the invention, but should be interpreted as merely exemplary of preferred embodiments. Those skilled in the art will envision other modifications within the scope and spirit of the present invention as defined by the following claims.

I claim:

1. A vessel loop having an outer surface adapted to frictionally engage a vessel of a patient, the loop comprising:
   an elongate elastomeric member having an axis extending between a firs tend and a second end; and
   a mesh carried by the elongate member and having portions disposed outwardly of the elongate member to form at least a portion of the outer surface of the vessel loop, the mesh having a generally fixed relationship with the elongate member and having properties for engaging the vessel and for increasing the frictional relationship with the vessel to inhibit migration of the vessel loop with respect to the vessel.

2. The vessel loop recited in claim 1 wherein the mesh is embedded in the outer surface of the elongate member.

3. The vessel loop recited in claim 1, wherein the mesh is formed of a non-elastomeric material.

4. The vessel loop recited in claim 1, wherein:
   the elongate member is generally flat in configuration and includes a first major surface and an opposing second major surface; and
   the mesh is disposed relative to at least one of the first major surface and the second major surface.

5. A vessel loop adapted to frictionally engage a vessel of the patient, the loop comprising:
   an elongate elastomeric member having an axis extending between a first end and a second end, and an outer surface adapted to engage the vessel;
   a mesh carried by the elongate member and disposed relative to the outer surface of the member, the mesh having a generally fixed relationship with the elongate member and having properties for increasing the frictional relationship with the vessel to inhibit migration of the vessel loop with respect to the vessel; and
   a sleeve disposed to surround the elongate element between the first end and the second end.

6. A vessel loop adapted to frictionally engage a vessel of the patient, the loop comprising:
   an elongate elastomeric member having an axis extending between a first end and a second end, and an outer surface adapted to engage the vessel;
   a mesh carried by the elongate member and disposed relative to the outer surface of the member, the mesh having a generally fixed relationship with the elongate member and having properties for increasing the frictional relationship with the vessel to inhibit migration of the vessel loop with respect to the vessel; and a hub disposed to maintain at least a portion of the mesh in a fixed relationship with the elongate member.

7. The vessel loop recited in claim 1 wherein the mesh is bonded to an outer surface of the elongate member.

8. The vessel loop recited in claim 7 wherein the bonded mesh is heatsealed to the outer surface of the elongate member.

9. The vessel loop recited in claim 7 wherein the bonded mesh is adhered to the outer surface of the elongate member.

10. A vessel loop having an outer surface adapted to frictionally engage a vessel of a patient, the loop comprising:
- an elongate member formed of an elastomeric material and having an axis extending between a first end and a second end;
- a mesh formed of a non-elastomeric material and being carried by the elongate member, the mesh being disposed to form at least a portion of the outer surface of the elongate member; and
- the mesh having properties for increasing the frictional relationship between the vessel and the elongate member in order to inhibit migration of the vessel loop with respect to the vessel.

11. The vessel loop recited in claim 10 wherein the mesh comprises at least one non-woven filament.

12. The vessel loop recited in claim 10 wherein the mesh includes at least one woven filament.

13. The vessel loop recited in claim 12 wherein the woven mesh has the configuration of a cylindrical sleeve and the sleeve is disposed to surround the elongate member.

14. The vessel loop recited in claim 13 wherein the elongate member is generally flat in radial cross-section and the outer surface of the vessel loop includes first and second opposed major surfaces.

15. The vessel loop recited in claim 13 wherein the elongate member has the configuration of a cylinder.

16. The vessel loop recited in claim 15 wherein the cylinder of the elongate member has a hollow configuration..

\* \* \* \* \*

UNITED STATES PATENT AND TRADEMARK OFFICE
CERTIFICATE OF CORRECTION

PATENT NO. : 6,030,394
DATED : February 29, 2000
INVENTOR(S) : Hart, Charles C.

It is certified that error appears in the above-identified patent and that said Letters Patent is hereby corrected as shown below:

column 4, line 24, after "between a", please delete "firs" and insert --first--.

Signed and Sealed this

Third Day of April, 2001

Attest:

NICHOLAS P. GODICI

*Attesting Officer*  *Acting Director of the United States Patent and Trademark Office*